United States Patent [19]

Maurer

[11] Patent Number: 5,171,333
[45] Date of Patent: Dec. 15, 1992

[54] METHANE PURIFICATION BY PRESSURE SWING ADSORPTION

[75] Inventor: Richard T. Maurer, Nanuet, N.Y.

[73] Assignee: UOP, Des Plaines, Ill.

[21] Appl. No.: 696,383

[22] Filed: May 6, 1991

Related U.S. Application Data

[63] Continuation-in-part of Ser. No. 462,514, Jan. 1, 1990, Pat. No. 5,013,334.

[51] Int. Cl.[5] ............................................. B01D 53/04
[52] U.S. Cl. ........................................ 55/26; 55/33; 55/62; 55/68; 55/74; 55/75
[58] Field of Search .................... 55/25, 26, 31, 33, 58, 55/62, 68, 74, 75

[56] References Cited

U.S. PATENT DOCUMENTS

| | | | |
|---|---|---|---|
| 2,882,244 | 4/1959 | Milton | 55/75 X |
| 2,988,503 | 6/1961 | Milton et al. | 55/75 X |
| 3,078,635 | 2/1963 | Milton | 55/75 X |
| 3,078,639 | 2/1963 | Milton | 55/75 X |
| 3,078,641 | 2/1963 | Milton | 55/75 X |
| 3,078,642 | 2/1963 | Milton | 55/75 |
| 3,078,644 | 2/1963 | Milton | 55/75 |
| 3,130,007 | 4/1964 | Breck | 23/113 |
| 3,176,444 | 4/1965 | Kiyonaga | 55/62 |
| 3,200,082 | 8/1965 | Breck et al. | 55/75 X |
| 3,430,418 | 3/1969 | Wagner | 55/25 |
| 3,564,816 | 2/1971 | Batta | 55/26 |
| 3,594,983 | 7/1971 | Yearout | 55/33 |
| 3,597,169 | 8/1971 | Savage | 55/75 X |
| 3,636,679 | 1/1972 | Batta | 55/62 X |
| 3,703,068 | 11/1972 | Wagner | 55/21 |
| 3,738,087 | 6/1973 | McCombs | 55/62 X |
| 3,986,849 | 10/1976 | Fuderer et al. | 55/25 |
| 4,240,986 | 12/1980 | Priegnitz | 55/75 X |
| 4,358,297 | 11/1982 | Eberly, Jr. | 55/75 X |
| 4,481,018 | 11/1984 | Coe et al. | 55/75 X |
| 4,503,023 | 3/1985 | Breck et al. | 423/328 |
| 4,544,378 | 10/1985 | Coe et al. | 55/75 X |
| 4,557,736 | 12/1985 | Sircar et al. | 55/75 X |
| 4,599,094 | 7/1986 | Werner et al. | 55/75 X |
| 4,717,398 | 1/1988 | Pearce | 55/75 X |
| 4,775,396 | 10/1988 | Rastelli et al. | 55/58 |
| 4,925,460 | 5/1990 | Coe et al. | 55/75 X |
| 5,013,334 | 5/1991 | Maurer | 55/62 X |

FOREIGN PATENT DOCUMENTS 55-030690 8/1980 Japan .

OTHER PUBLICATIONS

Molecular Sieve Zeolites, Advances in Chemistry, Ser. 101, American Chemical Society, Washington, D.C., 1971, p. 266.

*Primary Examiner*—Robert Spitzer
*Attorney, Agent, or Firm*—Thomas K. McBride; John G. Tolomei; Richard P. Silverman

[57] ABSTRACT

A process is provided for the separation of ethane from methane-containing feedstreams using pressure-swing adsorption wherein the adsorbent is a faujasite type of zeolitic aluminosilicate containing at least 20 equivalent percent of calcium cations or zinc cations or mixtures thereof and containing not more than 80 equivalent percent of alkali metal or alkaline earth metal cations.

18 Claims, 5 Drawing Sheets

Adsorption

Desorption

METHANE PURIFICATION BY PRESSURE SWING ADSORPTION

CROSS-REFERENCE TO RELATED APPLICATIONS

This application is a continuation-in-part of U.S. Ser. No. 462,514, filed Jan. 1, 1990 and issued May 7, 1991 as U.S. Pat. No. 5,013,334.

FIELD OF THE INVENTION

The present invention relates to processes for the separation of ethane from feedstreams containing mixtures thereof with methane. More particularly, the present invention relates to the use of particular cation types of zeolitic molecular sieve having the faujasite type of crystal structure as selective adsorbents in pressure swing adsorption processes for methane purification.

BACKGROUND OF THE INVENTION

Pressure swing adsorption (PSA) provides an efficient and economical means for separating a multi-component gas stream containing at least two gases having different adsorption characteristics. The more strongly adsorbable gas can be an impurity which is removed from the less strongly adsorbable gas which is taken off as product; or, the more strongly adsorbable gas can be the desired product, which is separated from the less strongly adsorbable gas. For example, it may be desired to remove carbon monoxide and light hydrocarbons from a hydrogen-containing feed stream to produce a purified (99+%) hydrogen stream for a hydrocracking or other catalytic process where these impurities could adversely affect the catalyst or the reaction. On the other hand, it may be desired to recover more strongly adsorbable gases, such as ethylene, from a feedstream to produce an ethylene-rich product.

In pressure swing adsorption, a multi component gas is typically fed to at least one of a plurality of adsorption zones at an elevated pressure effective to adsorb at least one component, while at least one other component passes through. At a defined time, the feedstream to the adsorber is terminated and the adsorption zone is depressurized by one or more cocurrent depressurization steps wherein pressure is reduced to a defined level which permits the separated, less strongly adsorbed component or components remaining in the adsorption zone to be drawn off without significant concentration of the more strongly adsorbed components. Then, the adsorption zone is depressurized by a countercurrent depressurization step wherein the pressure on the adsorption zone is further reduced by withdrawing desorbed gas countercurrently to the direction of feedstream. Finally, the adsorption zone is purged and repressurized. The final stage of repressurization is typically with product gas and is often referred to as product repressurization.

In multi-zone systems there are typically additional steps, and those noted above may be done in stages. U.S. Pat. Nos. 3,176,444 issued to Kiyonaga, 3,986,849 issued to Fuderer et al., and 3,430,418 and 3,703,068 both issued to Wagner, among others, describe multi-zone, adiabatic pressure swing adsorption systems employing both cocurrent and countercurrent depressurization, and the disclosures of these patents are incorporated by reference in their entireties.

Various classes of adsorbents are known to be suitable for use in PSA systems, the selection of which is dependent upon the feedstream components and other factors generally known to those skilled in the art. In general, suitable adsorbents include molecular sieves, silica gel, activated carbon and activated alumina. When PSA processes are used to purify hydrogen-containing streams, the hydrogen is essentially not adsorbed on the adsorbent. However, when purifying methane-containing streams, methane is often adsorbed on the adsorbent along with the impurity. The phenomenon is known in the PSA art as coadsorption.

The coadsorption of methane often causes a temperature rise in the adsorption zone due to the exothermic heat of adsorption which can be substantial, e.g., 40° F. or more. The degree of temperature rise depends, in part, upon the amount of methane present and the particular adsorbent employed. As is well known in the art, such a temperature can be undesirable since the equilibrium loading of many adsorbates, e.g., ethane, is reduced at higher temperatures. Hence it would be desirable to reduce such temperature rises during adsorption. Similarly, during PSA regeneration, the desorption of the coadsorbed methane along with the impurity often causes a temperature decrease of about the same magnitude as the previously mentioned temperature rise due to the endothermic heat of desorption. Also, as known in the art, such a temperature decrease during desorption can be undesirable since as noted above, the equilibrium loading of many adsorbates, e.g., ethane, is reduced at higher temperatures. Accordingly it would be desirable to reduce the temperature decreases often observed during desorption. However, as can be discerned from the above, the actual thermal behavior of the PSA system runs counter to what is desired. Nevertheless, a variety of processes have been proposed for purifying methane that utilize pressure swing adsorption.

U.S. Pat. No. 3,594,983 issued to Yearout et al., discloses a process for the removal of ethane and other hydrocarbons in a natural gas feedstream, i.e., methane, using a process that employs both pressure swing and thermal swing adsorption. The patentees recognized that zeolitic molecular sieves, e.g., 13X and 4A, were suitable for use in the process due to their high affinity for the impurity components. The patentees' apparent solution to the above-described thermal problem associated with methane coadsorption was to incorporate the thermal swing step into the adsorption process. That is, an adsorption zone that had been previously subjected to pressure reduction, i.e., PSA, was thereafter heated to desorb remaining impurities not removed by pressure swing.

Although not directly related to the separation of ethane from methane containing streams, U.S. Pat. No. 4,775,396 issued to Rastelli et al. discloses a PSA process for the bulk separation of $CO_2$ from methane, e.g., landfill gas. The patent discloses that for purification processes, $CO_2$ can be effectively removed from gas mixtures containing same using the calcium ion-exchanged form of zeolite A, but because of the strong affinity between the sorbent and adsorbate, thermal energy is required for effective desorption of the $CO_2$. However, for the bulk removal of $CO_2$ from methane, the patent discloses that PSA can be effective when using faujasite type of zeolitic aluminosilicate containing at least 20 equivalent percent of at least one cation species selected from the group consisting of zinc, rare earth, hydrogen and ammonium and containing not more than 80 equivalent percent of alkali metal or alkaline earth metal cations.

Japanese Patent No. 1039163, issued Mar. 31, 1981 to Union Carbide Corp., discloses a process for the purification of methane by the removal of ethane from a methane-containing feedstream that does not require the use of a thermal swing regeneration step. The patent discloses a PSA process that employs the use of silica gel as the adsorbent. The patent discloses that the silica gel adsorbent provides (1) high differential loading for all impurities to be removed from the product methane, (2) good enrichment of impurities in the waste gas, and (3) ease of cleaning of the bed with low pressure purge gas. It is further stated that high differential loadings permit relatively small adsorption zones which are low in cost and which reduce frequency of desorption, and hence reduce the product loss associated therewith. Enrichment of impurities in the waste gas reflects the degree of separation achievable in the process and is important in order to reject the impurities with minimum loss of product component. Ease of cleaning (or desorption) permits a high purity methane product to be obtained with an economically small quantity of purge gas. The above-identified characteristics stress the importance of achieving both high purity and high recovery of methane.

As noted in the above-identified Japanese patent, it is desirable to provide both high methane recoveries, i.e., minimum loss of product component, and high purity, i.e., low ethane content. Generally, however, there is an inverse relationship between purity and recovery and as such, processes have been operated to provide a high purity product at low recoveries or a low purity product at high recoveries. For example, it is not uncommon to obtain less than 50% methane recovery when purities are maintained at about 300 ppm ethane or less. Even at about 1000 ppm ethane in the product methane, typical processes may only achieve about 55% methane recovery. Accordingly, processes for the purification of methane are sought which can provide a high purity product at higher recoveries than heretofore possible.

SUMMARY OF THE INVENTION

By the present invention, a PSA process is provided for methane purification that can yield a high purity product at higher recoveries than heretofore possible. The process employs the use of a zeolitic molecular sieve that can effectively control the thermal problems associated with methane coadsorption yet provide suitable separation of impurity adsorbates.

In a broad aspect of the present invention there is provided a pressure swing adsorption process for the separation of ethane from a feedstream containing mixtures thereof with methane. The process includes the steps of a) passing the feedstream at an upper adsorption pressure to an adsorption zone containing a zeolitic molecular sieve of the faujasite type having a framework $SiO_2/Al_2O_3$ molar ratio of from 2 to 100 and containing at least 20 equivalent percent of calcium or zinc cations or mixtures thereof, and containing not more than 80 equivalent percent of alkali or alkaline earth metal cations other than calcium, or mixtures thereof, wherein ethane and methane are adsorbed and recovering an adsorption effluent stream enriched in methane relative to the feedstream; b) regenerating the adsorption zone by depressurizing the adsorption zone to a desorption pressure that is lower than the adsorption pressure, and recovering a desorption effluent stream containing ethane and methane; and c) repressurizing the adsorption zone to the adsorption pressure.

In another specific aspect of the present invention there is provided a pressure swing adsorption process for the separation of ethane from a feedstream containing mixtures thereof with methane. The process comprises the steps of a) passing the feedstream at an adsorption pressure of from about 100 to 500 psia to one of at least four adsorption zones containing a zeolitic molecular sieve of the faujasite type having a framework $SiO_2/Al_2O_3$ molar ratio of from 2 to 100 and containing at least 20 equivalent percent of calcium or zinc cations or mixtures thereof, and containing not more than 80 equivalent percent of alkali or alkaline earth metal cations other than calcium, or mixtures thereof; wherein ethane and methane are adsorbed and recovering an adsorption effluent stream enriched in methane relative to the feedstream, b) cocurrently depressurizing one adsorption zone and passing the effluent stream therefrom to another adsorption zone undergoing a repressurizing step as hereinafter described and equalizing the pressures therebetween; c) further cocurrently depressurizing the adsorption zone and passing the effluent stream therefrom as a purge gas stream to another adsorption zone undergoing a purging step as hereinafter described; d) countercurrently depressurizing the adsorption zone to a pressure of from about 14.7 to 50 psia and recovering a desorption effluent stream comprising ethane and methane; e) countercurrently purging the adsorption zone with the purge gas stream comprising the cocurrent depressurization effluent stream of step (c) from another adsorption zone and recovering a countercurrent purge effluent stream comprising ethane; f) repressurizing the adsorption zone by passing the cocurrent depressurization effluent stream of step (b) from another adsorption zone to the adsorption zone to equalize the pressures therebetween; g) further repressurizing the adsorption zone by passing a portion of the adsorption effluent stream from another adsorption zone thereto.

DETAILED DESCRIPTION OF THE INVENTION

The process of the present invention is useful for purifying methane-containing streams. In general, typical feedstreams will contain water up to saturation levels, less than 25 mol. % $C_2$–$C_5$ hydrocarbons, less than 30 mol. % carbon dioxide and less than 2 mol. % $C_6$ and higher hydrocarbons. Natural gas is a common source of such impurity-containing methane, and in natural gas the hydrocarbon impurities are primarily the saturated type such as ethane and propane. Additionally, natural gas can contain other components such as nitrogen, helium and argon, although such other components are not appreciably adsorbed in the process of the present invention. Preferably, the feedstream will contain from about 70 to 98 mol. % methane, from about 0.1 to 10 mol. % ethane, from about 0.1 to 10 mol. % $C_3+$ hydrocarbons and from about 0.1 to 20 mol. % $CO_2$. More preferably, the feedstream will comprise from about 75 to 95 mol. % methane, from about 0.5 to 10 mol. % ethane, from about 0.1 to 10 mol. % $CO_2$, and from about 0.1 to 5 mol. % $C_3+$ hydrocarbons.

The process is of the general PSA type wherein the methane feedstream is introduced at the highest pressure to the inlet end of an adsorption zone and the impurities are selectively adsorbed in each of at least two sequentially operated adsorption zones. Impurity-depleted methane is discharged from the adsorption zone so that impurity adsorption fronts are formed in the zone at the feedstream inlet end and progressively move toward the purified methane discharge end. Preferably, the impurity-depleted methane product recovered as an adsorption effluent contains less than about 2000 ppm of ethane and more preferably less than 300 ppm. The feedstream flow is terminated when the impurity adsorption fronts are at a predetermined point between the zone inlet and discharge ends. Impurity-depleted methane gas is then preferably released from the adsorption zone discharge end thereby cocurrently depressurizing the adsorption zone to lower pressure in one or more stages. The adsorption zone is then countercurrently depressurized to the lowest desorption pressure to remove the adsorbed impurities and adsorbed methane. The depressurized zone is purged of the impurities by flowing one part of the impurity-depleted methane gas from another adsorption zone countercurrently therethrough from the discharge end to the inlet end. The purged zone is at least partially repressurized by another adsorption zone prior to the introduction of the feedstream to the inlet end. The term "cocurrent" denotes that the direction of gas flow is cocurrent to the direction of gas flow during the adsorption step. Similarly, the term "countercurrent" denotes that the gas flow is countercurrent to the direction of gas flow during the adsorption step.

The faujasite type of zeolite employed in the practice of the present invention can be either of the type X or the type Y. Zeolite X and the method for its preparation is described in detail in U.S. Pat. No. 2,882,244 issued Apr. 14, 1959 to R. M. Milton. The $SiO_2/Al_2O_3$ molar ratio of zeolite X is from about 2 up to 3. In the as synthesized form, zeolite Y has a $SiO_2/Al_2O_3$ molar ratio of from greater than 3 up to 6. The method for synthesizing zeolite Y is disclosed in detail in U.S. Pat. No. 3,130,007 issued Apr. 21, 1964 to D. W. Breck. The forms of zeolite Y which contain molar $SiO_2/Al_2O_3$ values greater than 6 can be prepared by several dealumination techniques well known in the art. For example, high temperature steaming treatments which result in dealumination are reported by P. K. Maher et al. in MOLECULAR SIEVE ZEOLITES, Advan. Chem. Ser. 101, American Chemical Society, Washington, D.C., 1971, p. 266. A more recently reported procedure, especially useful for increasing $SiO_2/Al_2O_3$ of zeolite Y, involves dealumination and the substitution of silicon into the dealuminated lattice sites. This process is disclosed in U.S. Pat. No. 4,503,023 issued Mar. 5, 1985 to Skeels et al. As used herein, the term "faujasite type of structure" means the framework structure, irrespective of chemical composition, distrubution of the different T-atoms, cell dimensions and symmetry, designated as "FAU" in the ATLAS OF ZEOLITE STRUCTURE TYPES, W. M. Meier and D. H. Olsen, Published by the Structure Commission of the International Zeolite Association (1978).

In order to be useful in the process of the present invention, the faujasite zeolite must be treated in order to have a framework $SiO_2/Al_2O_3$ molar ratio of from 2 to 100 and containing at least 20 equivalent percent of one or a mixture of two or more cation species selected from the group consisting of zinc, rare earth, hydrogen, ammononium and calcium and containing not more than 80 equivalent percent of alkali or alkaline earth metal cations other than calcium or mixtures thereof.

Preferably, the framework $SiO_2/Al_2O_3$ ratio of the zeolitic molecular sieve is from 2 to 20 and the zeolitic molecular sieve contains at least 20 equivalent percent of one or a mixture of two or more of zinc, rare earth, hydrogen, ammonium and calcium cations.

It is further preferred that the zeolitic molecular sieve contains at least 40 equivalent percent of one or a mixture of two or more of zinc, rare earth, hydrogen, ammonium and calcium cations and less than 40 equivalent percent of alkali and alkaline earth metal cations other than calcium. When Zeolite X is employed as the adsorbent, it is preferred that zinc cations be used as an ion-exchange cation. When Zeolite Y is employed as the adsorbent, it is preferred that calcium cations be used as an ion-exchange cation. The various ion-exchange techniques and the like which can be used to prepare the faujasite zeolites of the present invention are well known to those skilled in the art and need not be further described herein.

In addition to the faujasite zeolite, it may be desirable in certain instances to employ another adsorbent in the adsorption zone in order to remove some of the feedstream impurities prior to separating ethane from methane with the faujasite zeolites. For instance, it may be desirable to utilize an adsorbent bed of silica gel, activated carbon or alumina, or combinations thereof, to adsorb the $C_3+$ hydrocarbon fraction or water. The use of such adsorbents and appropriate selection thereof can be determined by those skilled in the art. Those skilled in the art will further recognize that other adsorbents in addition to those specifically enumerated above can be used in accordance with the present invention in combination with the faujasite zeolite.

In accordance with the present invention, the adsorption pressure is generally from about 50 to 1000 psia and preferably from about 100 to 500 psia. The desorption pressure is generally from about 1 to 100 psia and preferably from about 14.7 to 50 psia. Suitable operating temperatures are generally within the range of from about 50°-150° F. There can be a variety of cocurrent depressurization steps to intermediate pressures, cocurrent purging steps and countercurrent purging steps, all of which are well known to those skilled in the art and described in. the previously cited patents relating to PSA processes. For example, three or more of such cocurrent depressurization steps can be employed for pressure equalization to further improve product recovery such as disclosed in the above-identified U.S. Pat. No. 3,986,849. In addition, the purge step can be performed either prior to, simultaneously with, or subsequently to the regenerating or desorption step by passing a methane-containing stream countercurrently through the adsorption zone and recovering a countercurrent purge effluent stream comprising ethane. The methane-containing stream can comprise a portion of the adsorption effluent product stream. However, it is generally preferred that at least a portion of one or more of the cocurrent depressurization effluent streams be employed as the methane-containing stream, i.e., purge gas. Moreover, the process of the present invention may be practiced with essentially any adiabatic pressure swing process such as the multi zone adsorption systems described in Fuderer et al., U.S. Pat. No. 3,986,849, the four adsorption zone systems described in Wagner, U.S. Pat. No. 3,430,418 and Batta, U.S. Pat. No. 3,564,816, the three adsorption zone systems described in Batta, U.S. Pat. No. 3,636,679, and the two adsorption zone systems described in McCombs, U.S. Pat. No. 3,738,087, the disclosures of which are hereby incorporated by reference.

The selection of the appropriate PSA process configuration and operating conditions can be determined by those skilled in the art. For instance, those skilled in the art will recognize that performing the adsorption step at an excessively high pressures, i.e., which depend upon the particular system and can be determined by experimentation, can produce non-self-cleaning conditions and a large, abrupt increase in $C_2+$ content in the product.

As used herein, the term "self cleaning" is used in connection with impurity enrichment. Self-cleaning is evidenced by a stable impurity front which does not progressively encroach upon the product end of the adsorption zone as numerous repetitive cycles proceed. If the adsorption zone is not self-cleaning with respect to an impurity, then the impurity will eventually appear in the effluent stream from the product end of the adsorption zone and upon continued cycling, its concentration in the product will gradually increase. In general, operating at lower pressures during adsorption favors a product of higher purity (lower $C_2+$ content). However, as the adsorption pressure is reduced relative to the purge pressure, differential loading on the adsorbent decreases and adsorption zone size tends to increase (or cycle time must be shorter). This increases the fraction of product lost in blowdown and required for purging, and recovery of methane is reduced.

The process of the present invention will hereinafter be described with reference to the drawings.

Figure 1:
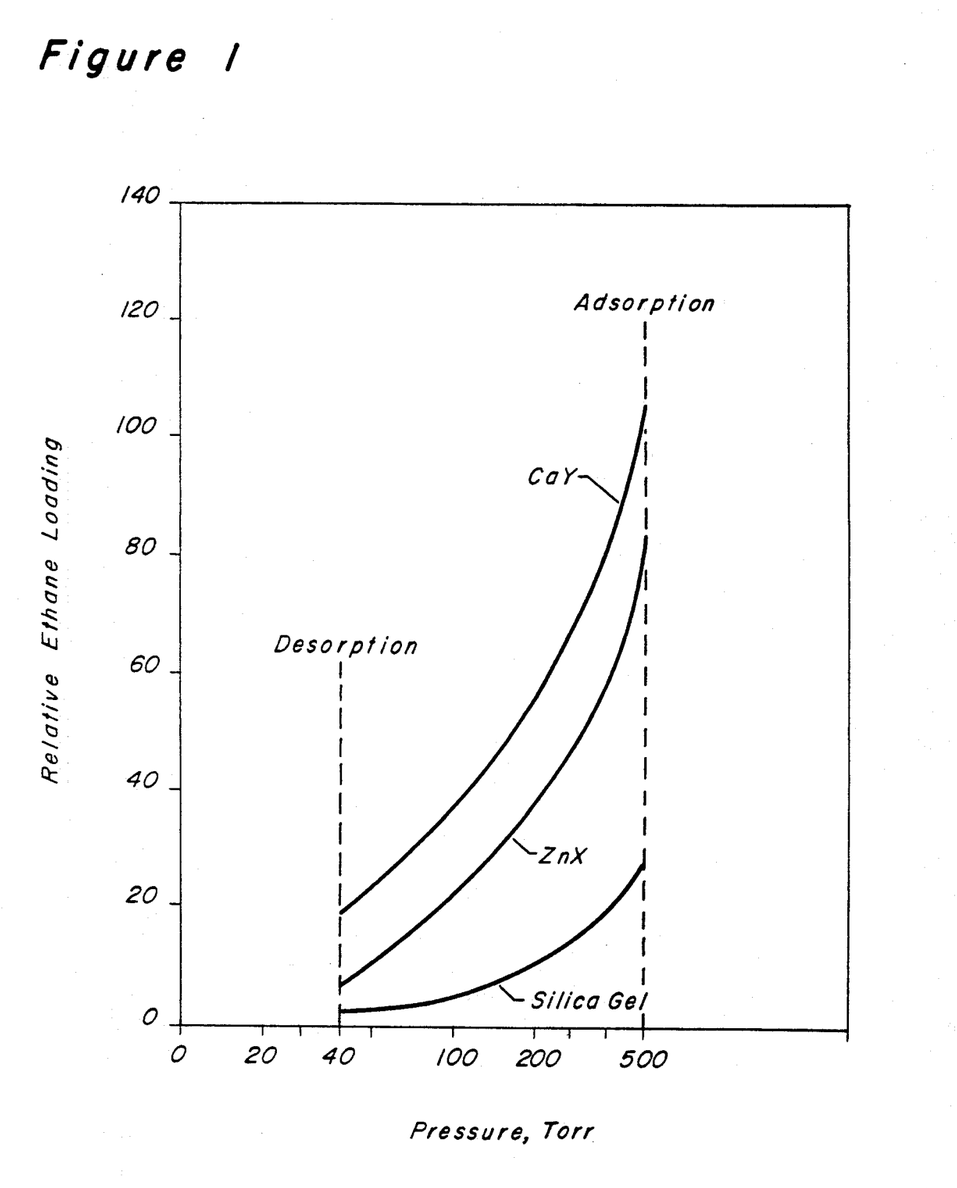
FIG. 1 illustrates the recovery and purity for the separation of ethane from methane.

To further describe the role of the adsorbent in this process and its selectivity for adsorbing ethane at various pressures, FIG. 1 illustrates the relative ethane loading as a pure component for zinc X, calcium Y and silica gel adsorbents in a PSA bed over a range of pressure on the x-axis equivalent to the range of pressure between the desorption step at low pressure and the adsorption step at high pressure. The differences between the high pressure of the adsorption step and the low pressure of the desorption step indicate the relative loading for ethane over the particular adsorbent material. Table 1 shows that at the process conditions of a typical PSA operation, zinc X and calcium Y both possess a greater difference between ethane loadings over the pressure range of operation than does silica gel. This difference is often called the delta loading for a particular component and it indicates the relative amount of working capacity in the PSA bed for the pressure swing operation. As shown in the table, the delta loading for zinc X of 75 was about three times that of the silica gel at 26 and the delta loading for calcium Y of 87 was about 3.3 times that of the silica gel. In general, the greater the delta loading, the greater the working capacity of the bed and the better performance in the PSA system. Furthermore, these pure component data indicate that both zinc X and calcium Y should have a similar working capacity for ethane which would be greater than the silica gel alone over these same conditions in a multicomponent system.

TABLE 1
PSA BED DELTA LOADING FOR PURE ETHANE ADSORPTION

| Adsorbent | Ethane Loading At End of Adsorption Step | Ethane Loading At End of Desorption Step | Delta Ethane Loading |
|---|---|---|---|
| Type R-Silica Gel | 29 | 3 | 26 |
| Zinc X | 82 | 7 | 75 |
| Calcium Y | 105 | 18 | 87 |

The pure component data in FIG. 1 represent data at a total pressure equal to the partial pressure of ethane over the adsorbent. Thus, in the operation of a PSA system processing a mixture of methane and ethane, the partial pressure of ethane will be reduced significantly. Therefore, an experiment was set up to evaluate the performance of these adsorbents relative to the performance of the silica gel adsorbent.

Figure 2:
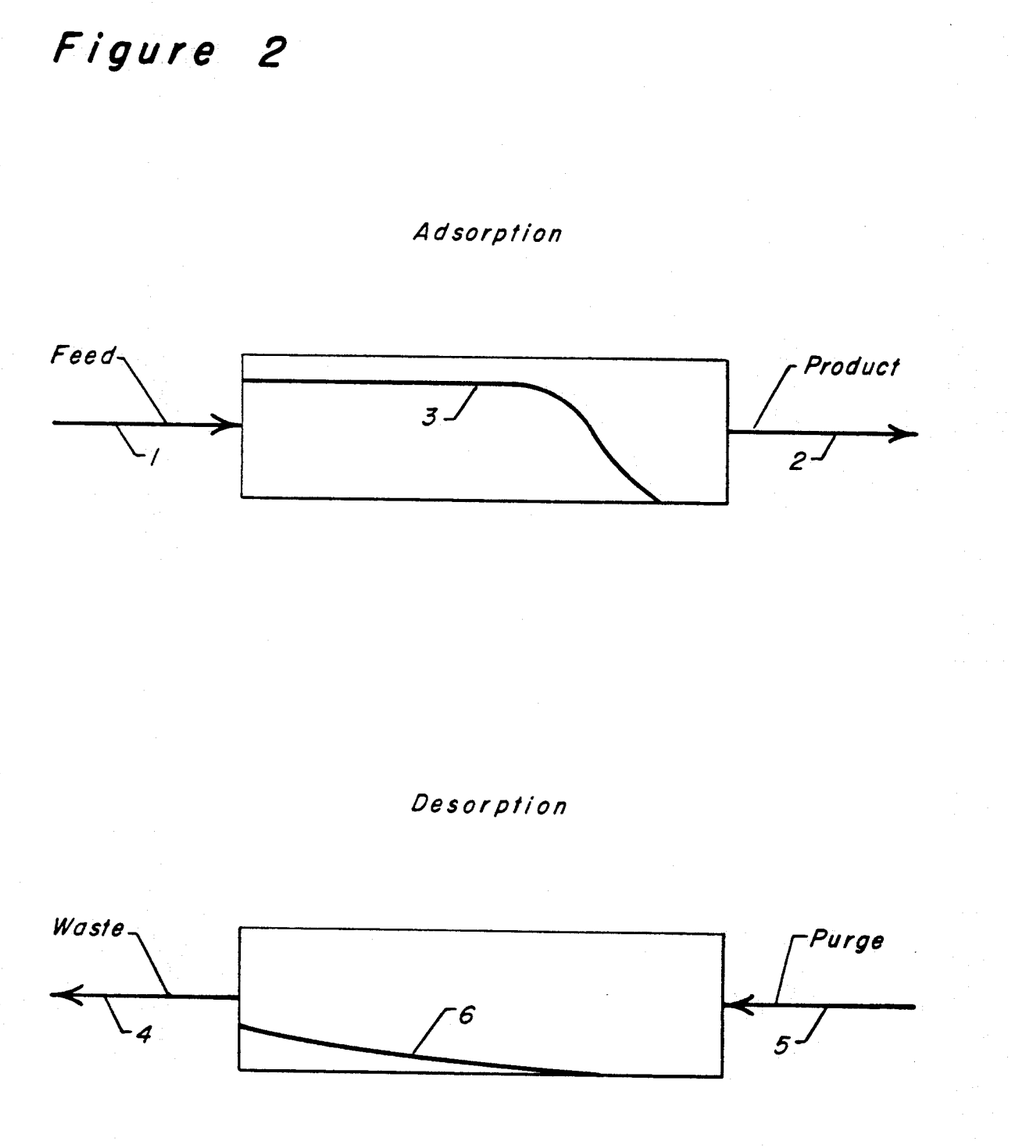
FIG. 2 is a schematic flowsheet of a four bed PSA system.

FIG. 2 illustrates the composition profile of ethane as the partial pressure of ethane which is the total pressure of the system multiplied by the molar fraction of ethane in the bed at the end adsorption and at the end of the desorption cycles in the PSA bed. During the adsorption step wherein the adsorption of ethane is taking place at high pressure as the feed (1) is introduced, the ethane profile (3) in the bed is at its maximum. As methane product (2) is withdrawn, the ethane profile (3) moves toward the product end of the bed. During the desorption step at low pressure the ethane rich material is rejected from the bed as waste (4) and the partial pressure of ethane (6) is reduced to its lowest level as purge gas (5) is introduced.

Figure 3:
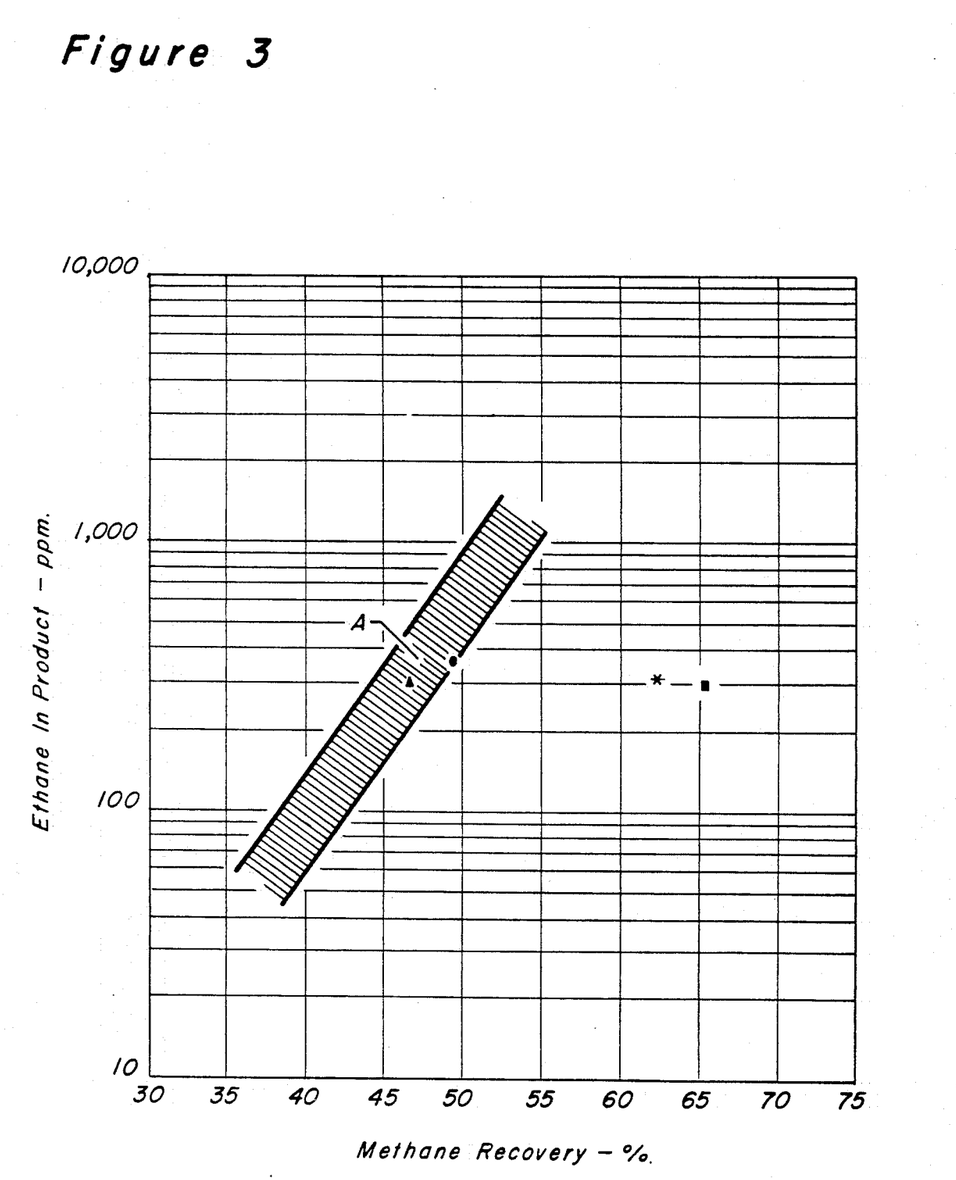
FIG. 3 is a chart illustrating the relative adsorption loading of ethane at a pure component over a range of pressure for zinc X, calcium Y and silica gel adsorbents.

FIG. 3 illustrates the recovery and purity relationship for the separation of ethane from methane. The shaded area, designated curve A, was reproduced from FIG. 5 of Japanese Patent No. 1039163 hereinbefore described and represents the typical variation of product purity with methane recovery observed by the patentees using silica gel adsorbent.

The data represented by the round data point shows typical performance obtained by applicant when separating a feedstream containing about 6 mol. % ethane, balance methane, using silica gel adsorbent in a PSA test cycle having the steps of; adsorption at a pressure of about 130 psia, cocurrent depressurization to a pressure of about 70 psia, cocurrent depressurization to a pressure of about 33 psia, cocurrent depressurization to a pressure of about 26 psia, countercurrent depressurization to a pressure of about 16 psia, countercurrent purge with product methane and repressurization to 130 psia. A single bed adsorption zone was used for the testing and had a length of 5.9 ft. and an internal volume of 0.03 $ft^3$, i.e., about 850 cc. The adsorption zone was insulated to approximate adiabatic operation. The adsorption zone was loaded with silica gel adsorbent which is generally commercially available and can be obtained from UOP, Des Plaines, Ill.

The data represented by the square data point illustrates the unexpectedly enhanced results by replacing the 850 cc silica gel adsorption zone with a zinc-exchanged zeolite X containing about 84 equivalent percent $Zn^{+2}$ cations in accordance with the present invention. The zinc-exchanged zeolite X can also be obtained from UOP, Des Plaines, Ill. The PSA test cycle and testing unit were the same as described above. It can be seen that for an ethane level of about 300 ppm in the product gas, the methane recovery was about 29% higher, i.e., 66% versus 51%, than with the silica gel.

Enhanced results were also observed when about 25 vol. %, i.e., about 212 cc, of the silica gel adsorbent from the effluent end of the adsorption zone was replaced with zinc-exchanged Zeolite X. The PSA test cycle and testing unit were the same as described above. At 300 ppm ethane in the product gas, the recovery of methane was about 60% for the combined silica gel-ZnX adsorption zone.

Recalling the trends in FIG. 1 for the calcium-exchanged zeolite Y and their similarity with that of the zinc-exchanged zeolite X a series of tests were performed in the simple bed adsorption zone for a partial loading of the calcium-exchanged zeolite Y with silica gel to verify the performance for the multicomponent separation system. Approximately 25 vol. % of the effluent end of the adsorption zone was replaced with calcium-exchanged zeolite Y containing about 90 equivalent percent calcium cations and the balance of the adsorption zone was silica gel. The calcium-exchanged zeolite calcium Y can also be obtained from UOP, Des Plaines, Ill. Although the density of the CaY material was 20% lower than the ZnX material resulting in a lower amount of calcium cations on a weight basis than the equivalent volume of the zinc X adsorbent, the calcium-exchanged zeolite Y provide equally enhanced results. As in the PSA cycle test with the zinc-exchanged zeolite X, for an ethane level of 300 ppm in the product gas, the recovery of methane was 57%, or about 12% higher than the methane recovery for silica gel alone.

Figure 4:
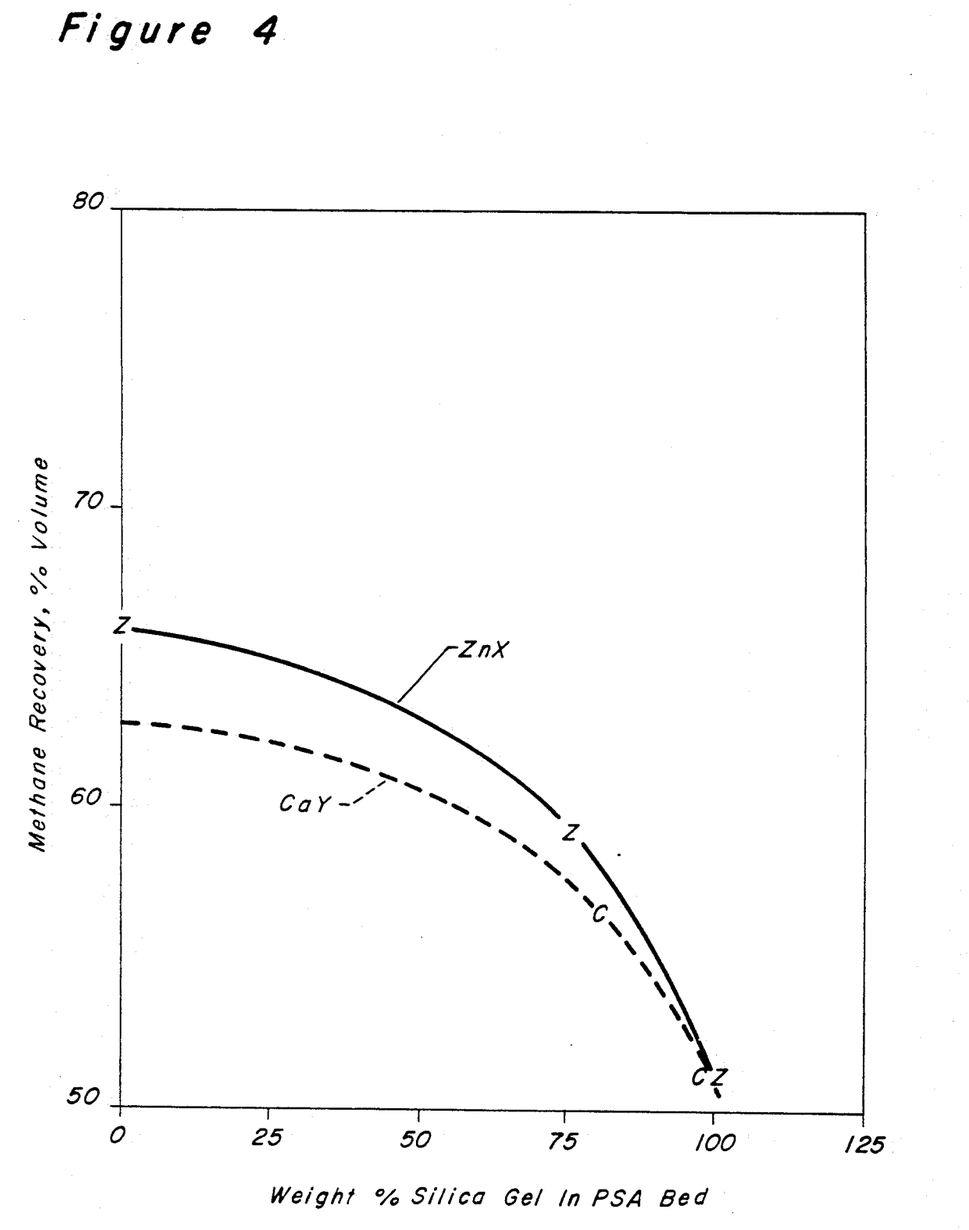
FIG. 4 is a schematic design illustrating the composition profile of ethane in a PSA bed during the adsorption and desorption steps.

This experiment verified that the pure component adsorption trends relative to the ZnX were valid for the CaY adsorbent even though the bed contained a smaller amount of calcium-exchanged zeolite on a weight basis. FIG. 4 presents the performance of the PSA unit on a weight percentage of silica gel in the bed for both the ZnX and the CaY zeolite adsorbents. The performance data as measured by methane recovery in percent is plotted against the weight percent of silica gel in the bed. Each adsorbent has the base point for 100% silica gel in common at 51% methanol recovery. The performance curve (1) described by the ZnX material reaches a 67% recovery when the bed is 100% ZnX. On the basis of the performance of the CaY material at slightly less than 25% of the bed and its pure component relationship to the ZnX performance, the performance of the CaY material at 100% of the bed will range between 57 and 63% or more likely between 61 to 63% methane recovery. Referring to FIG. 3, the data indicated by the star is representative of the PSA operating with the bed operating with 100% CaY as developed from the above analysis.

Hence, it is possible to obtain a substantial improvement in performance even when only a portion of the adsorption zone contains the adsorbent material of the present invention.

The data in FIG. 3 represented by the triangular data point is presented for comparison purposes and illustrates the expected results using a faujasite that is not characterized in accordance with the present invention. As determined by mathematical simulation of a PSA cycle as described above, the expected performance using a sodium-exchanged zeolite X, i.e., 13X, is about the same or worse than that of silica gel.

Figure 5:
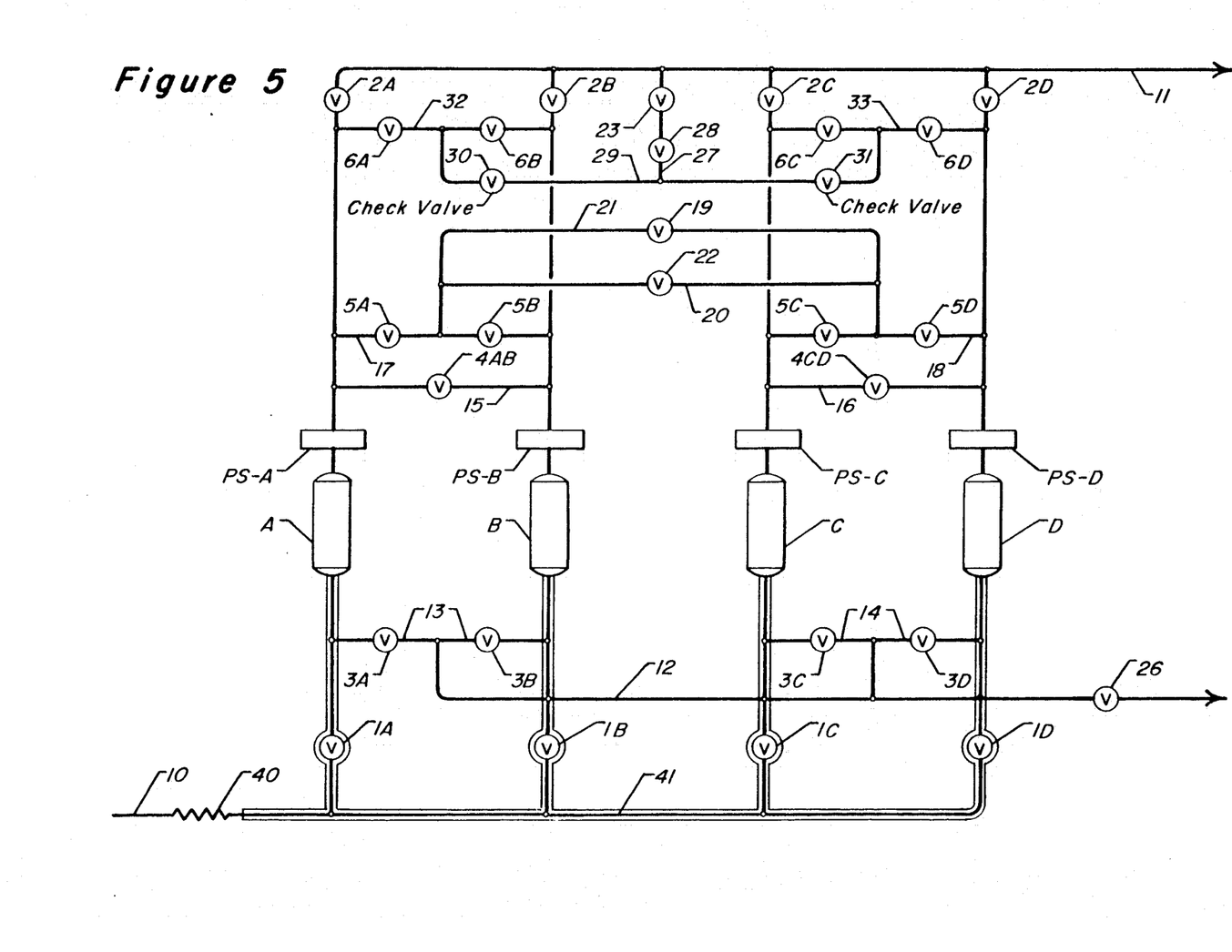
FIG. 5 illustrates the recovery of methane in the PSA system as a function of the amount of silica gel in the PSA bed.

FIG. 5 is a schematic flowsheet of a four-adsorption zone PSA system. With reference to FIG. 5, the four adsorption zones are loaded with a zinc cation-exchanged zeolite X adsorbent obtained from UOP, Des Plaines, Ill. The four adsorption zones are arranged in parallel between feedstream manifold 10 and product manifold 11. Feed is introduced to manifold 10 and passed through a heater 40 before entering feed header 41. Feed to, and product from the adsorption zones are controlled respectively by automatic valves 1A-D and 2A-D. A high pressure equalization step is accommodated by connecting conduits 15 and 16 containing respectively automatic valves 4AB and 4CD. Cocurrent depressurization for purge is accomplished through manifolds 17 and 18 containing respectively automatic valves 5A-B and 5C-D together with cross-over conduit 20 containing manual trim valve 22. A low pressure equalization step is accomplished through cross-over conduit 21 which also connects manifolds 17 and 18 and contains automatic valve 19. Flow from the adsorption zones through manifolds 13 and 14 to waste manifold 12 is controlled by automatic valves 3A-D. Product for final repressurization of the adsorption zones returns through conduit 27 containing regulating valves 23 and 28, then flows through repressurization manifold 29 containing check valves 30 and 31, and finally passes through one of manifolds 32 and 33 containing respectively automatic valves 6A-B and 6C-D.

The full cycle will be described for Adsorption zone A and is typical for all adsorption zones. Pressures and times are illustrative. Assume adsorption zone A is pressurized and that all its associated valves are initially closed. Valves 1A and 2A open and feedstream at 157 psia flows from feedstream manifold 10 to the adsorption zone, and product flows from the adsorption zone into manifold 11. Flow continues at steady feedstream pressure for 5 minutes. Now valves 1A and 2A close and valve 4AB opens, thereby establishing flow between adsorption zone A and adsorption zone B which has been partially repressurized and is initially at 30 psia pressure. The adsorption zones equalize in pressure at 97 psia in 0.75 minute. It is important to note that due to pressure drop through the apparatus, the actual pressure in the two adsorption zones may, in fact, not be exactly equal. Differences in the actual pressures are expected and are within the scope of the present invention. Next, valve 4AB closes and valves 5A, 5C, 3C and 26 open to establish flow between adsorption zones A and C through manifold 20. Adsorption zone C has just completed countercurrent blowdown and is now purged by gas from adsorption zone A which is throttled by valve 22 to about 23 psia. Purge continues for 3.5 minutes when adsorption zone A pressure drops to 37 psia. PS-A, PS-B, PS-C, and PS-D are pressure switches which sense the terminal pressure in beds A-D, respectively. The terminal pressure is sensed by a pressure switch PS-C which is actuated to close valve 3C and open valve 19. Flow continues from adsorption zone A to adsorption zone C but now adsorption zone C is dead-ended so that pressures equalize at 30 psia in 0.75 minute. Valves 5A, 5C, 19 and 26 close and valve 3A opens, thus releasing residual pressure in adsorption zone A countercurrently through waste manifold 12. The final pressure, 23 psia, is set by a regulating valve (not shown) downstream in waste conduit 12, which delivers the gas to a fuel header. Valve 26 is a resistance valve rather than a shut-off valve and when closed, imposes a flow restriction which prevents excess flow velocities in adsorption zone A. Countercurrent depressurization is complete in 0.75 minute after which, valve 26, 5A and 5D open. This allows purge gas to flow from adsorption zone D through manifold 20 to adsorption zone A at about 23 psia, then through waste manifold 12. Purge continues for 3.5 minutes.

Adsorption zone A has completed its adsorption phase, its product recovery phase and its desorption phase. It is now ready to begin a three-step repressurization sequence. Valve 3A closes and flow from adsorption zone D continues but with adsorption zone A dead-ended so that pressures equalize at 30 psia in 0.75 minute. Valve 6A also opens to simultaneously permit product from manifold 11 to return through valves 23 and 28 to adsorption zone A. Now valves 5A and 5D close and valve 4AB opens. This establishes communication with adsorption zone B which initially is at feedstream pressure (157 psia), and the two adsorption zones equalize at 97 psia in 0.75 minute. Finally, valve 4AB closes and only product from manifold 11 continues to flow to adsorption zone A. The pressure in adsorption zone A reaches substantially feedstream pressure (157 psia) in 4.25 minute.

This completes a full 20-minute cycle for adsorption zone A which is now ready to receive the feedstream for the adsorption stroke by closing valve 6A and opening valves 1A and 2A. The cycle for adsorption zone A is typical for all adsorption zones A–D, and the adsorption zones are placed on adsorption sequentially in ¼-cycle phase relationship such that the feedstream and product flows are continuous.

The above-described process sets forth a four-adsorption zone five-step cycle containing two pressure equalization steps. Alternatively, this process may be practiced in a variety of other cycles as hereinbefore described without departing from the scope of the claims that follow.

What is claimed is:

1. A pressure swing adsorption process for the separation of ethane from a feedstream comprising mixtures thereof with methane, said process comprising:
   a) passing the feedstream at an upper adsorption pressure through an adsorption zone containing a zeolitic molecular sieve of the Y type having a framework $SiO_2/Al_2O_3$ molar ratio of from 2 to 100 and containing at least 20 equivalent percent of calcium cations and containing not more than 80 equivalent percent of alkali or alkaline earth metal cations other than calcium, or mixtures thereof, wherein ethane and methane are adsorbed and recovering an adsorption effluent stream enriched in methane relative to the feedstream;
   b) regenerating the adsorption zone by depressurizing the adsorption zone to a desorption pressure, said desorption pressure being lower than said adsorption pressure, and recovering a desorption effluent stream comprising ethane and methane; and
   c) repressurizing the adsorption zone to the adsorption pressure.

2. The process of claim 1 wherein said depressurizing is performed in a direction countercurrent to said passing of said feedstream through said adsorption zone.

3. The process of claim 2 which further includes at least one cocurrent depressurization step performed prior to said regenerating step comprising cocurrently depressurizing the adsorption zone to a pressure intermediately between the adsorption pressure and the desorption pressure and recovering a cocurrent depressurization effluent stream comprising methane.

4. The process of claim 3 which includes three or more cocurrent depressurization steps.

5. The process of claim 2 which further includes a countercurrent purge step performed either prior to, simultaneously with, or subsequently to said regenerating step, comprising passing a methane-containing purge gas countercurrently through said adsorption zone and recovering a countercurrent purge effluent stream comprising ethane.

6. The process of claim 2 wherein said process includes a first and second adsorption zone and said repressurizing step comprises passing at least a portion of one of the adsorption effluent stream or the cocurrent depressurization effluent streams or both from said first adsorption zone to said second adsorption zone.

7. The process of claim 1 wherein the framework $SiO_2/Al_2O_3$ ratio of the zeolitic molecular sieve is from 2 to 20.

8. A process according to claim 7 wherein the zeolitic molecular sieve contains at least 40 equivalent percent of calcium cations and less than 40 equivalent percent of alkali and alkaline earth metal cations other than calcium or mixtures thereof.

9. The process of claim 1 wherein the feedstream additionally comprises at least one component selected from the group consisting of $C_3+$ hydrocarbons, $CO_2$, $H_2O$ and mixtures thereof.

10. The process of claim 9 wherein the feedstream comprises from about 70 to 98 mol. % methane, from about 0.1 to 10 mol. % ethane, from about 0.1 to 10 mol. % $C_3+$ hydrocarbons, and from about 0.1 to 20 mol. % $CO_2$.

11. The process of claim 9 wherein said components are adsorbed on the zeolitic molecular sieve.

12. The process of claim 9 wherein the adsorption zone further comprises at least two adsorbents wherein one adsorbent is selected from the group consisting of silica gel, alumina, and activated carbon.

13. The process of claim 1 wherein the adsorption pressure is from about 100 to 500 psia.

14. The process of claim 1 wherein the desorption pressure is from about 14.7 to 50 psia.

15. A pressure swing adsorption process for the separation of ethane from a feedstream comprising mixtures thereof with methane, said process comprising:
   a) passing the feedstream at an adsorption pressure of from about 100 to 500 psia to one of at least four adsorption zones containing a zeolitic molecular sieve of the Y type having a framework $SiO_2/Al_2O_3$ molar ratio of from 2 to 100 and containing at least 20 equivalent percent of calcium cations and containing not more than 80 equivalent percent of alkali or alkaline earth metal cations other than calcium, or mixtures thereof; wherein ethane and methane are adsorbed and recovering an adsorption effluent stream enriched in methane relative to the feedstream;
   b) cocurrently depressuring said one adsorption zone and passing the effluent stream therefrom to another adsorption zone undergoing a repressuring step as hereinafter described and equalizing the pressures therebetween;

c) further cocurrently depressurizing said one adsorption zone and passing the effluent stream therefrom as purge gas to another adsorption zone undergoing a purging step as hereinafter described;

d) countercurrently depressurizing said one adsorption zone to a pressure of from about 14.7 to 50 psia and recovering a desorption effluent stream comprising ethane and methane;

e) countercurrently purging said one adsorption zone with a purge gas comprising the cocurrent depressurization effluent stream of step (c) from another adsorption zone and recovering a countercurrent purge effluent stream comprising ethane;

f) repressurizing said one adsorption zone by passing the cocurrent depressurization effluent stream of step (b) from another adsorption zone to the adsorption zone to equalize the pressures therebetween; and g) further repressurizing said one adsorption zone by passing a portion of the adsorption effluent stream from another adsorption zone thereto.

16. The process of claim 15 wherein the feedstream comprises from about 75 to 95 mol. % methane, from about 0.5 to 10 mol. % ethane, from about 0.1 to 10 mol. % $CO_2$ and about 0.1 to 5 mol. % $C_3+$ hydrocarbons.

17. The process of claim 16 wherein the adsorption effluent stream comprises less than about 2000 ppm ethane.

18. The process of claim 17 wherein the adsorption effluent stream comprises less than about 300 ppm ethane.

* * * * *